(12) United States Patent
Kawamura et al.

(10) Patent No.: US 11,833,287 B2
(45) Date of Patent: Dec. 5, 2023

(54) AIR TRAP CHAMBER AND EXTRACORPOREAL CIRCULATION CIRCUIT

(71) Applicant: NIKKISO CO., LTD., Tokyo (JP)

(72) Inventors: Shunsuke Kawamura, Makinohara (JP); Ryo Kato, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 589 days.

(21) Appl. No.: 17/049,927

(22) PCT Filed: Mar. 15, 2019

(86) PCT No.: PCT/JP2019/010961
§ 371 (c)(1),
(2) Date: Oct. 22, 2020

(87) PCT Pub. No.: WO2019/211952
PCT Pub. Date: Nov. 7, 2019

(65) Prior Publication Data
US 2021/0046238 A1     Feb. 18, 2021

(30) Foreign Application Priority Data
May 2, 2018   (JP) ................................ 2018-088658

(51) Int. Cl.
*A61M 1/36*      (2006.01)
*B01D 19/00*    (2006.01)
*A61M 5/36*      (2006.01)

(52) U.S. Cl.
CPC ....... *A61M 1/3638* (2014.02); *B01D 19/0031* (2013.01); *A61M 1/3627* (2013.01);
(Continued)

(58) Field of Classification Search
None
See application file for complete search history.

(56) References Cited

U.S. PATENT DOCUMENTS 5,849,065 A * 12/1998 Wojke ................. A61M 1/3627
96/219
8,500,672 B2   8/2013 Caleffi et al.
(Continued)

FOREIGN PATENT DOCUMENTS

EP         0 728 509 A2    8/1996
JP        H09-000808 A    1/1997
(Continued)

OTHER PUBLICATIONS

Dec. 16, 2021 Extended European Search Report issued in European Application No. 19796958.7.
(Continued)

*Primary Examiner* — Gabriel E Gitman
(74) *Attorney, Agent, or Firm* — Oliff PLC

(57) ABSTRACT

An air trap chamber is provided with a chamber body and a filter. An introduction pipe of the chamber body is provided so as to extend to the inside of the chamber body, and an inlet port which is an end opening of the introduction pipe is provided, on the inner circumferential surface of the chamber body, so as to be directed toward the circumferential direction. The filter is provided inside the chamber body, and covers an outlet port of the chamber body. Openings are formed, at multiple stages along the center axis direction, in the cylindrical portion of the filter. An opening at an upper stage on the ceiling portion side of the filter has a circumferential width greater than that of an opening at a lower stage on the outlet port side.

3 Claims, 17 Drawing Sheets

(52) U.S. Cl.
CPC ........... *A61M 5/36* (2013.01); *A61M 2205/75* (2013.01); *A61M 2205/7545* (2013.01); *A61M 2206/16* (2013.01); *B01D 19/0057* (2013.01)

(56) References Cited

U.S. PATENT DOCUMENTS

| | | | |
|---|---|---|---|
| 8,641,657 B2 * | 2/2014 | Ribolzi | A61M 1/3622 |
| | | | 210/497.1 |
| 2006/0173395 A1 | 8/2006 | Brugger et al. | |

FOREIGN PATENT DOCUMENTS

| | | |
|---|---|---|
| JP | 3066867 U | 3/2000 |
| JP | 2001-309975 A | 11/2001 |
| JP | 2010-119561 A | 6/2010 |
| JP | 2013-090675 A | 5/2013 |
| WO | 2008/065472 A1 | 6/2008 |

OTHER PUBLICATIONS

Oct. 31, 2022 Office Action Issued in Chinese Patent Application No. 201980028250.7.
May 21, 2019 Office Action issued in Japanese Patent Application No. 2018-088658.
May 28, 2019 International Search Report issued in International Patent Application No. PCT/JP2019/010961.
May 11 2023 Office Action issued in Chinese Patent Application No. 201980028250.7.

* cited by examiner

AIR TRAP CHAMBER AND EXTRACORPOREAL CIRCULATION CIRCUIT

TECHNICAL FIELD

The present invention relates to an air trap chamber and an extracorporeal circulation circuit including the air trap chamber.

BACKGROUND

For instance, in hemodialysis, blood removed from a patient is sent to an extracorporeal circulation circuit. The extracorporeal circulation circuit includes an arterial side circuit to which the removed blood is supplied, a purifier (dialyzer) that purifies the blood sent from the arterial side circuit, and a venous side circuit that returns the purified blood to the patient.

At least one of the arterial side circuit and the venous side circuit is provided with an air trap chamber for capturing bubbles in blood flowing through the circuit (debubbling). For instance, the air trap chamber has an inlet and an air vent at the upper end and an outlet at the lower end.

Further, the air trap chamber is provided with a filter that covers the outlet and captures solid matters such as thrombus. For instance, Patent Document 1 discloses a filter provided with a cylindrical body, and a dome-shaped top head provided at the upper end of the body.

In the body of the filter, openings in multiple stages are formed along the central axis C1 of the cylinder. Regarding the openings, in Patent Document 1, a filter is provided such that the longitudinal width along the central axis of an opening in an upper stage adjacent to the top head is larger than the longitudinal width of an opening in a lower stage adjacent to the outlet. Hence, the resistance (flow resistance) at the (longitudinal) opening in the upper stage is reduced, thereby supressing the retention of the flow in the air trap chamber.

CITATION LIST

Patent Literature

Patent Document 1: U.S. Pat. No. 8,500,672 B1

SUMMARY

Technical Problem

It is an object of the present invention to provide an air trap chamber capable of making the resistance of a liquid passing through a filter lower than in hitherto-used techniques.

Solution to Problem

The present invention relates to an air trap chamber. The air trap chamber includes a chamber body and a filter. The chamber body has a substantially cylindrical shape, and an inlet pipe is provided at one end with respect to the direction of the central axis and an outlet is provided at the other end, and a liquid flows down from the inlet pipe to the outlet. The inlet pipe extends into the chamber body, and an inlet, which is an end opening of the inlet pipe, is provided at the inner circumferential surface of the chamber body and faces in the circumferential direction. The filter is provided in the chamber body and covers the outlet of the chamber body. The filter has a cylindrical section that surrounds the outlet and extends in the direction of the central axis of the chamber body, and a ceiling section that covers the upper end of the cylindrical section opposite to the lower end of the chamber body adjacent to the outlet. In the cylindrical section of the filter, openings in multiple stages aligned in the direction of the central axis are formed. The circumferential width of the opening in the upper stage adjacent to the ceiling section of the filter is made larger than the circumferential width of the opening in the lower stage adjacent to the outlet.

With this configuration, the inlet of the chamber body is faced to the inner circumferential surface of the chamber body and faces in the circumferential direction, so that the flow of the liquid flowing from the inlet swirls along the inner circumferential surface of the chamber body. The flow velocity of the swirl flow generally decreases toward the center of rotation, so that, around the filter (outlet), the flow velocity above the filter becomes relatively low with increasing distance from the inner circumferential surface of the chamber body. Therefore, as in the above configuration, when the width in the direction of the swirl flow; that is, the circumferential direction, of the opening in the upper stage of the filter, is widened relative to the circumferential width of the opening in the lower stage, the resistance of a liquid passing through the upper stage of the filter can be suppressed.

In the aforementioned invention, the filter may be provided with multiple ribs, extending in the direction of the central axis, aligned along the circumferential direction. In this case, the multiple ribs may include a first rib extending from the lower end of the filter to the ceiling section of the filter, and a second rib extending from the lower end of the filter and terminating before reaching the ceiling section of the filter.

With the second rib, the circumferential width of the opening above the end point of the second rib can be made larger than the circumferential width of the opening below the end point.

In the aforementioned invention, the filter may be provided with multiple ribs, extending in the direction of the central axis, aligned along the circumferential direction. In this case, the ribs may be formed so that the circumferential width decreases from the lower end of the filter toward the ceiling section of the filter.

With a rib shape that tapers toward the upper side, the circumferential width of a relatively higher opening can be made larger than the circumferential width of a relatively lower opening.

The present invention also relates to an extracorporeal circulation circuit. The removed blood is circulated in the circuit. The air trap chamber according to the aforementioned invention is coupled to the flow path of the extracorporeal circulation circuit.

Advantageous Effects of Invention

According to the present invention, the resistance of a liquid passing through a filter can be made lower than in hitherto-used techniques.

DESCRIPTION OF EMBODIMENTS

Figure 1:
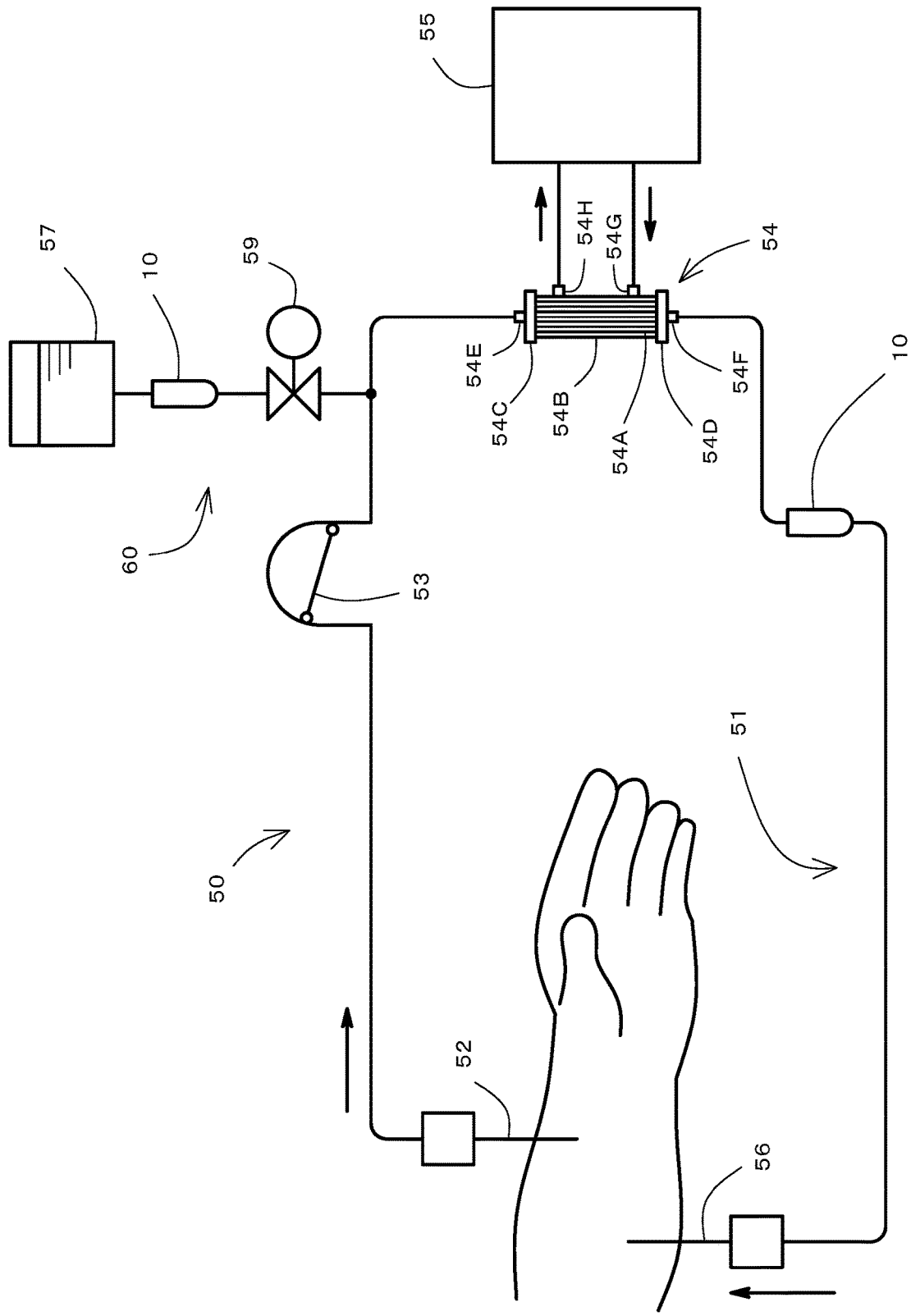
FIG. 1 is a diagram illustrating an extracorporeal circulation circuit using an air trap chamber according to an embodiment of the present invention.

FIG. 1 illustrates an extracorporeal circulation circuit to which an air trap chamber 10 according to an embodiment is coupled. The extracorporeal circulation circuit is a circuit used for hemodialysis, for example, and includes an arterial side circuit 50, a blood purifier 54, a dialyzer 55, a venous side circuit 51, and a replacement liquid line 60. Note that the air trap chamber 10 according to the embodiment is coupled, to the extracorporeal circulation circuit used for dialysis treatment, but this is not necessarily the case. For instance, the air trap chamber 10 according to the embodiment may be coupled to an extracorporeal circulation circuit that circulates blood removed from a patient and can perform purification treatment. For instance, the air trap chamber 10 according to the embodiment may be coupled to an extracorporeal circulation circuit used in acetate free biofiltration (AFBF), continuous slow hemofiltration therapy, hemoadsorption therapy, selective blood cell depletion therapy, simple plasma exchange therapy, double membrane filtration plasma exchange therapy, plasma adsorption therapy, or the like. The air trap chamber 10 according to the embodiment can be provided in the arterial side circuit 50, the venous side circuit 51, and the replacement liquid line 60, which will be described later, of the extracorporeal circulation circuit. In addition, the air trap chamber 10 according to the embodiment can be coupled to a path where thrombus may occur; that is, an extracorporeal circulation circuit path in which blood or blood components flow. In addition, the air trap chamber 10 according to the embodiment can be coupled to extracorporeal circulation circuit paths in which blood or blood components flow, extracorporeal circulation circuit paths in which saline solution flows, and extracorporeal circulation circuit paths including these.

The arterial side circuit 50 is supplied with blood removed from the patient's body. The arterial side circuit 50 includes an arterial side puncture needle 52 and a roller pump 53 from the upstream side. The arterial side puncture needle 52 is introduced into a blood vessel of the patient and the blood is sent to the tube of the arterial side circuit 50 (blood removal).

The roller pump 53 transports the blood in the tube to the blood purifier 54 by externally squeezing the tube. For instance, since the circuit may be filled with a priming liquid from the venous side circuit during priming, the roller pump 53 may be capable of rotating in the forward and reverse directions.

The air trap chamber 10 according to this embodiment may be coupled between the arterial side puncture needle 52 and the roller pump 53 and between the roller pump 53 and the blood purifier 54. The configuration and function of the air trap chamber 10 will be described later. It should be noted that the air trap chamber 10 in the venous side circuit 51 is indispensable to make sure to debubble the blood to be returned, whereas these air trap chambers 10 provided in the arterial side circuit 50 are optional.

The replacement liquid line 60 is provided between the roller pump 53 and the blood purifier 54 in the arterial side circuit 50. The replacement liquid line 60 is provided with a replacement liquid bag 57 and a clamp 59. The air trap chamber 10 is provided between the replacement liquid bag 57 and the clamp 59.

The replacement liquid bag 57 contains saline solution as a replacement liquid. For instance, during priming of the extracorporeal circulation circuit, the clamp 59 is opened and the saline solution is supplied from the replacement liquid bag 57 to the extracorporeal circulation circuit. Bubbles in the circuit are removed by filling the circuit with saline solution. Upon completion of the priming, the clamp 59 is closed.

Upon completion of the dialysis treatment, the clamp 59 is opened again to return the blood from the circuit to the patient's body, filling the circuit with saline solution from the replacement liquid bag 57. In other words, the blood in the circuit is replaced with saline solution.

The blood purifier 54 purifies the blood sent from the arterial side circuit 50. The blood purifier 54 is a so-called dialyzer, and the dialysate and blood are exchanged through a hollow fiber membrane 54A, for example. In the blood purifier 54, a bundle of the hollow fiber membranes 54A (hollow fiber membrane bundle) is contained in a column 54B.

The column 54B is a cylindrical container member, and has an inlet side cap 54C at one end with respect to the direction of the central axis and an outlet side cap 54D at the other end. The inlet side cap 54C is provided with a blood inlet port 54E coupled to a connector (not shown in the drawing) at the downstream end of the arterial side circuit 50. The outlet side cap 54D is provided with a blood outlet port 54F coupled to a connector (not shown in the drawing) at the upstream end of the venous side circuit 51. Blood sent from the arterial side circuit 50 flows from the blood inlet port 54E into the hollow fiber membranes 54A.

A dialysate inlet port 54G is provided in a portion of the column 54B adjacent to the outlet side cap 54D. A dialysate outlet port 54H is provided in a portion of the column 54B adjacent to the inlet side cap 54C. The dialysate is sent from the dialyzer 55 into the column 54B through the dialysate inlet port 54G. The dialysate and blood are exchanged via the hollow fiber membranes 54A, thereby purifying the blood. The dialysate after the exchange is returned to the dialyzer 55 via the dialysate outlet port 54H. The purified blood is sent to the venous side circuit 51 via the blood outlet port 54F.

In the venous side circuit 51, the purified blood is returned to the patient's body via a venous side puncture needle 56. The air trap chamber 10 is provided in the venous side circuit 51 in order to remove bubbles in the blood (debubble) when the blood is returned.

Figure 2:
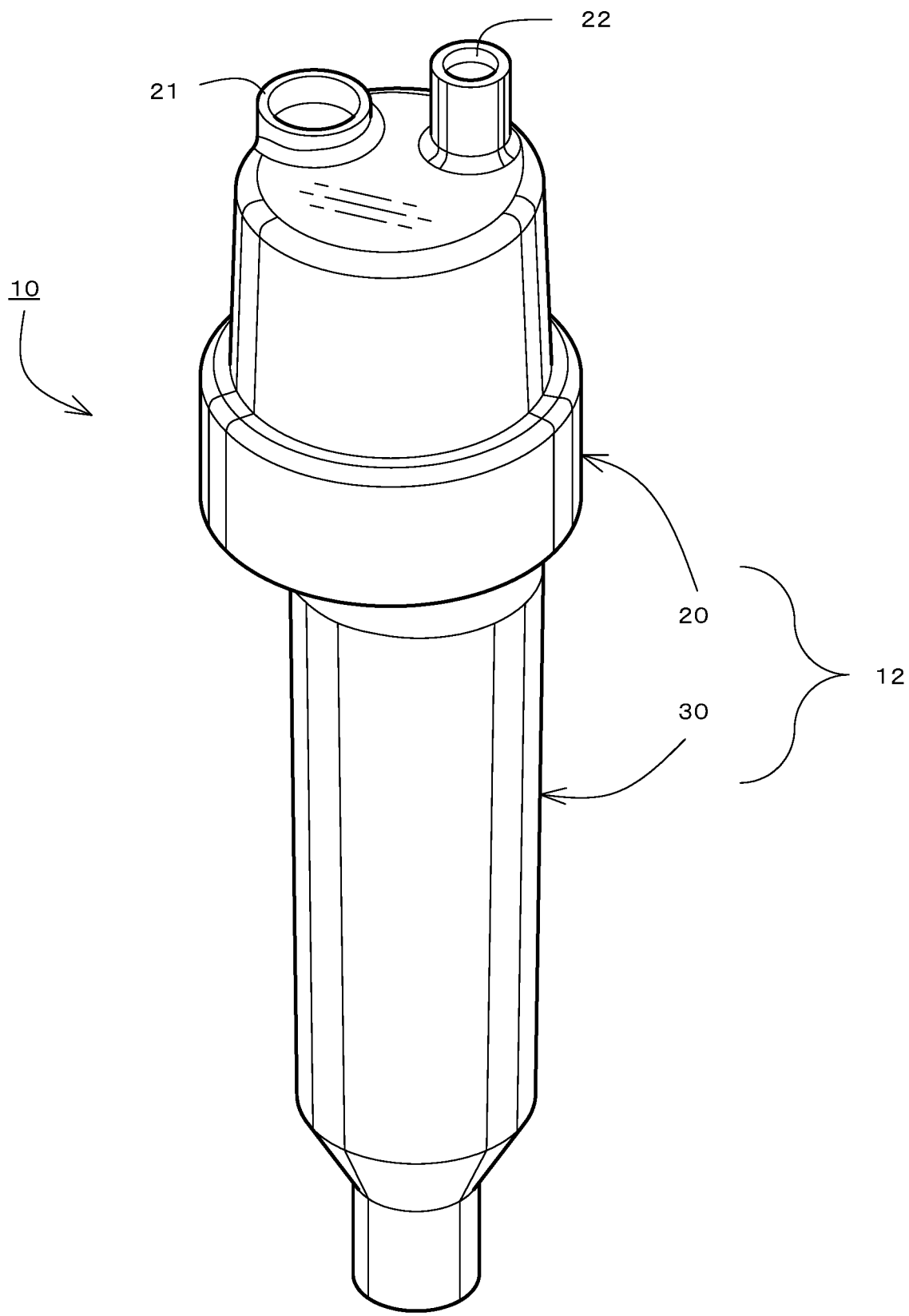
FIG. 2 is a perspective view illustrating an air trap chamber according to the embodiment.
Figure 3:
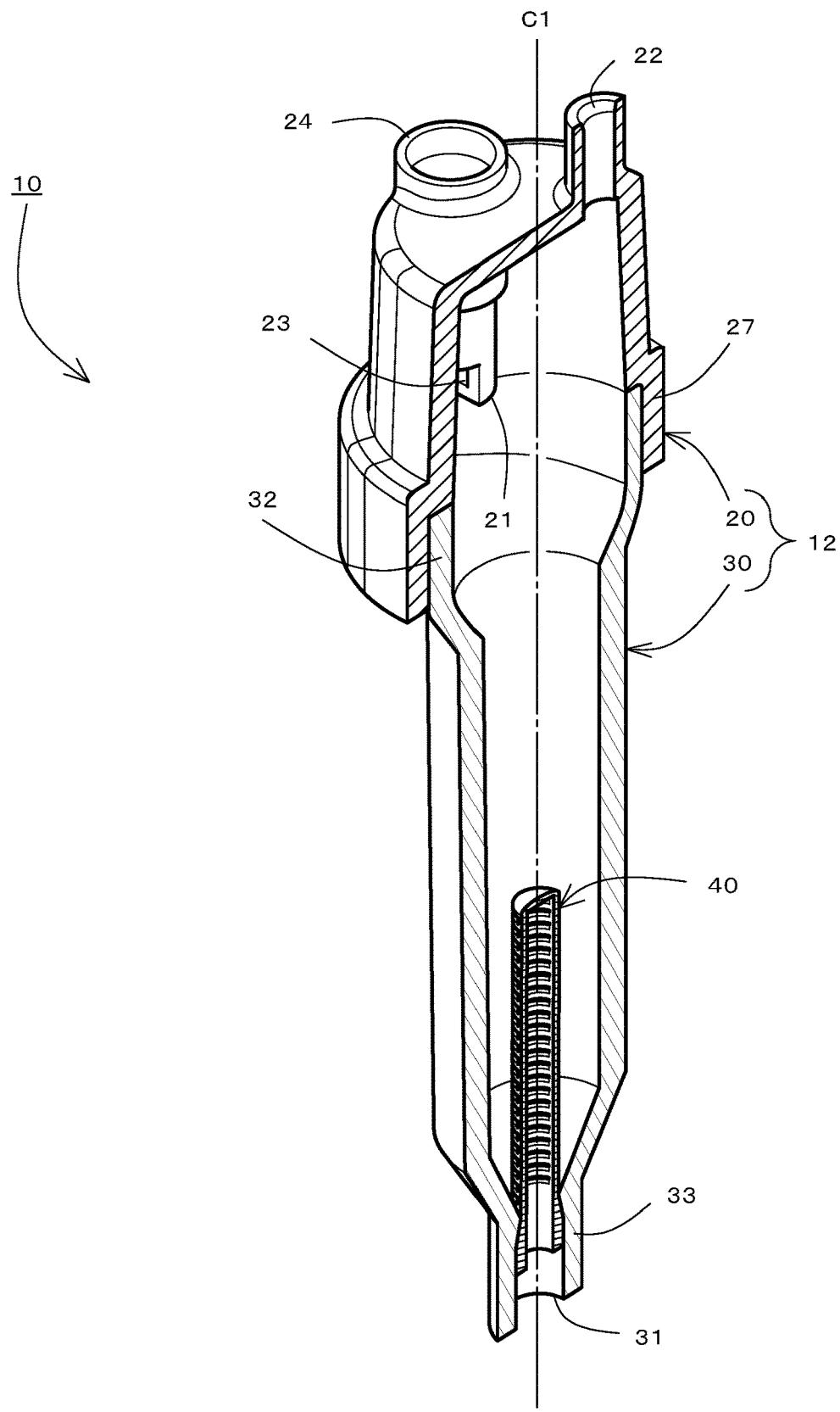
FIG. 3 is a perspective sectional view illustrating an air trap chamber according to the embodiment.

FIG. 2 illustrates the air trap chamber 10 according to this embodiment. FIG. 3 illustrates a perspective sectional view of the air trap chamber 10. The air trap chamber 10 includes a chamber body 12 and a filter 40.

During the dialysis treatment, the air trap chamber 10 is used upright so that its upper side in the drawing is the upper side and its lower side in the drawing is the lower side. Unless otherwise specified, the position and configuration of each component will be described below with reference to the upright posture during use.

The chamber body 12 has a substantially cylindrical shape, and an inlet pipe 21 and an air vent 22 are provided at one end (upper end) with respect to the direction of a central axis C1. An outlet 31 is provided at the other end (lower end) with respect to the direction of the central axis C1. In other words, in the chamber body 12, a liquid (for example, blood or saline solution) flows down from the inlet pipe 21 to the outlet 31. When the central axes of a cap 20 and a housing 30 that constitute the air trap chamber 10 are misaligned from the central axis C1, the central axis C1 may be the central axis C1 of the housing 30, which occupies most of the volume of the chamber body 12.

The chamber body 12 may consist of, for example, the cap 20 and the housing 30. The cap 20 and the housing 30 are obtained by, for example, injection molding a resin. The cap 20 is an upper member of the chamber body 12, and is a member having a U-shaped cross section provided with the inlet pipe 21 and the air vent 22.

Figure 4:
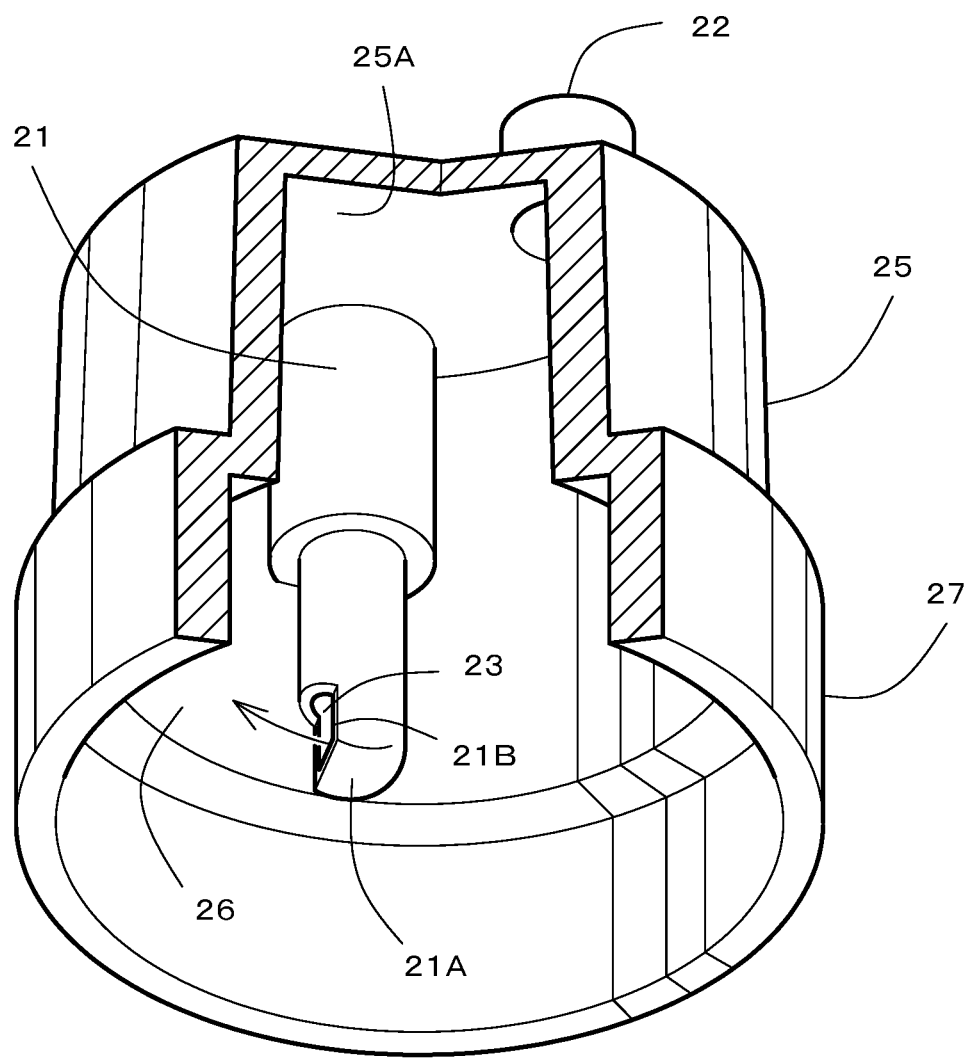
FIG. 4 is a diagram illustrating a structure of a cap of the air trap chamber according to the embodiment.

FIG. 4 illustrates a perspective sectional view of the cap 20. The cap 20 includes a cap body 25, a flange 27, and the inlet pipe 21. The cap body 25 has a cylindrical shape whose upper end is closed by a top wall 25A and whose lower end is coupled to the flange 27. The air vent 22 passes through the top wall 25A in the thickness direction.

The inlet pipe 21 is extended from the top wall 25A to the inside of the cap body 25; that is, the inside of the chamber body 12. An inlet 23 is formed at the lower end of the inlet pipe 21. Since the inlet 23 is provided below the top wall 25A in this way, when the air trap chamber 10 is provided in the venous side circuit 51, a bubble leak, a phenomenon in which bubbles in the chamber body 12 leak from the inlet pipe 21 to the upstream side of the venous side circuit 51, can be prevented.

In other words, for instance, when the inlet 23 is provided at the lower surface of the top wall 25A; that is, at the same height as the air vent 22, the bubbles in the chamber may move to the inlet 23 without going to the air vent 22, and then leak to the upstream side of the venous side circuit 51. For this reason, in the air trap chamber 10 according to this embodiment, the inlet 23 is lowered to the inside of the chamber to prevent mixing of air bubbles into the upstream side of the venous side circuit 51.

The inlet 23 is provided along an inner circumferential surface 26 of the cap body 25, and an opening is faced in the circumferential direction of the inner circumferential surface 26. For instance, a lower wall 21A is formed at the lower end of the inlet pipe 21 and its side wall is cut out, forming the inlet 23. For instance, the inlet 23 is faced parallel to the tangential direction of the inner circumferential surface 26. The cut surface 21B of the inlet 23 is formed so as to be parallel to the radial direction of the inner circumferential surface 26.

Since the inlet 23 is provided at the inner circumferential surface of the cap body 25 and faced in the circumferential direction, the flow of the liquid (for example, blood or saline solution) flowing out from the inlet 23 becomes a swirl flow along the inner circumferential surface 26. Since the liquid flow in the air trap chamber 10 becomes a swirl flow, the retention of the liquid in the air trap chamber 10 is suppressed as compared with the case where a specific flow is not formed.

The flange 27 is coupled to the lower end of the cap body 25. The inner diameter of the flange 27 is made larger (increased) than the inner diameter of the cap body 25. Referring to FIG. 3, a flange 32 of the housing 30 is inserted into the flange 27. For instance, an adhesive is encapsulated between the inner circumferential surface of the flange 27 of the cap 20 and the outer circumferential surface of the flange 32 of the housing 30 so that the cap 20 and the housing 30 are bonded to each other.

The housing 30 is a substantially cylindrical member having the flange 32 at the upper end and an outlet pipe 33 at the lower end. For example, the inner diameter of the flange 32 may be equal to the inner diameter of the cap body 25 (see FIG. 4).

The inner diameter of the housing 30 is narrower at the bottom and coupled to the outlet pipe 33. The outlet 31 is formed at the lower end of the outlet pipe 33, and is coupled to the tube of the venous side circuit 51 by adhesion or the like. The filter 40 is provided to cover the outlet pipe 33. The detailed configuration will be described later.

Figure 5:
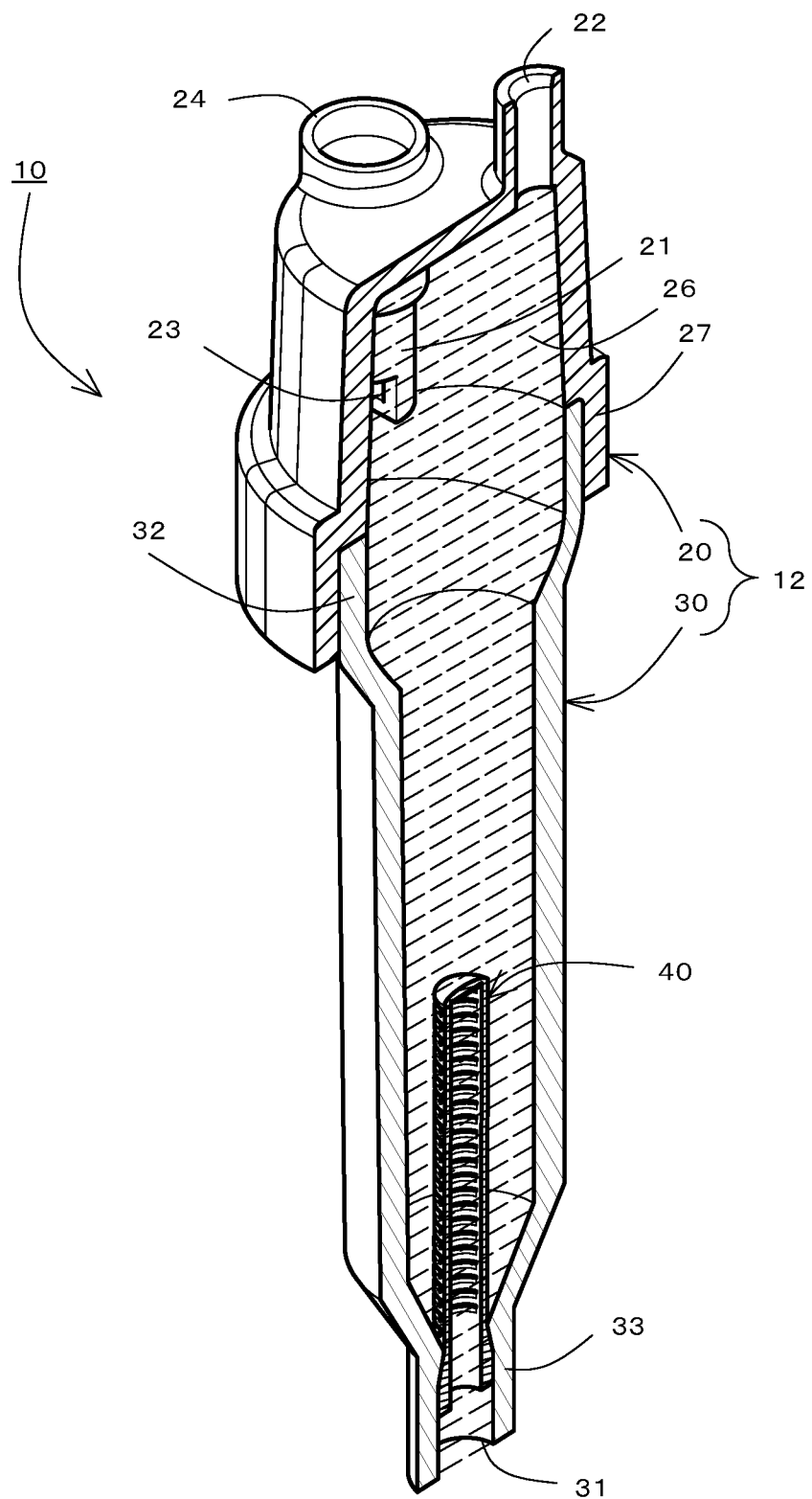
FIG. 5 is a perspective sectional view illustrating the air trap chamber according to the embodiment during use.

FIG. 5 illustrates the state of the air trap chamber 10 during dialysis treatment. The air trap chamber 10 may be a so-called airless chamber in which almost the entire internal space of the chamber body 12 is filled with a liquid (for example, blood or saline solution) as shown by the hatching in the drawing.

Figure 6:
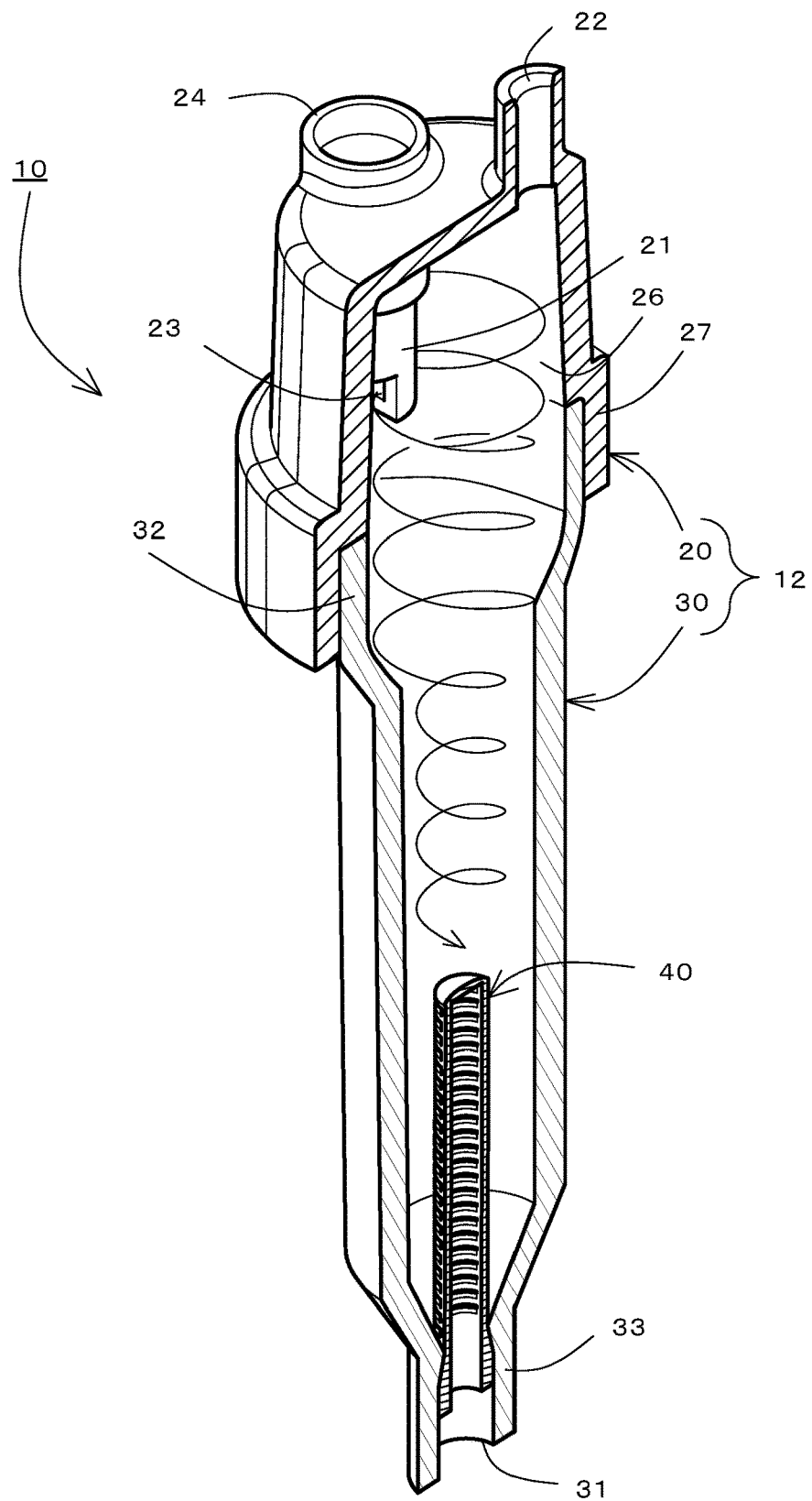
FIG. 6 is a diagram illustrating the overall flow in the air trap chamber according to the embodiment.

With the chamber body 12 filled with the liquid as described above, the liquid further flows in through the inlet 23. Since the inlet 23 is provided at the inner circumferential surface 26 of the cap 20 and faced in the circumferential direction as described above, the flow of the liquid flowing from the inlet 23 becomes a swirl flow along the inner circumferential surface 26 as illustrated in FIG. 6. The liquid in the chamber body 12 is sent from the outlet 31 to the venous side circuit 51 via the filter 40 while maintaining the state of the swirl flow.

Since the swirl flow has a lower flow velocity toward the swirl center, the liquid above the filter 40 away from the inner circumferential surface; i.e., provided on the swirl axis, has a lower flow velocity (flow rate) than the flow near the inner circumferential surface of the chamber body 12. As will be described later, in the air trap chamber 10 according to this embodiment, the upper opening of the filter 40 has a larger circumferential opening width than does the lower one. Hence, the permeation resistance (flow resistance) of a liquid passing through the upper opening is reduced, and the retention of the liquid having a low flow rate (low flow velocity) is suppressed.

Figure 7:
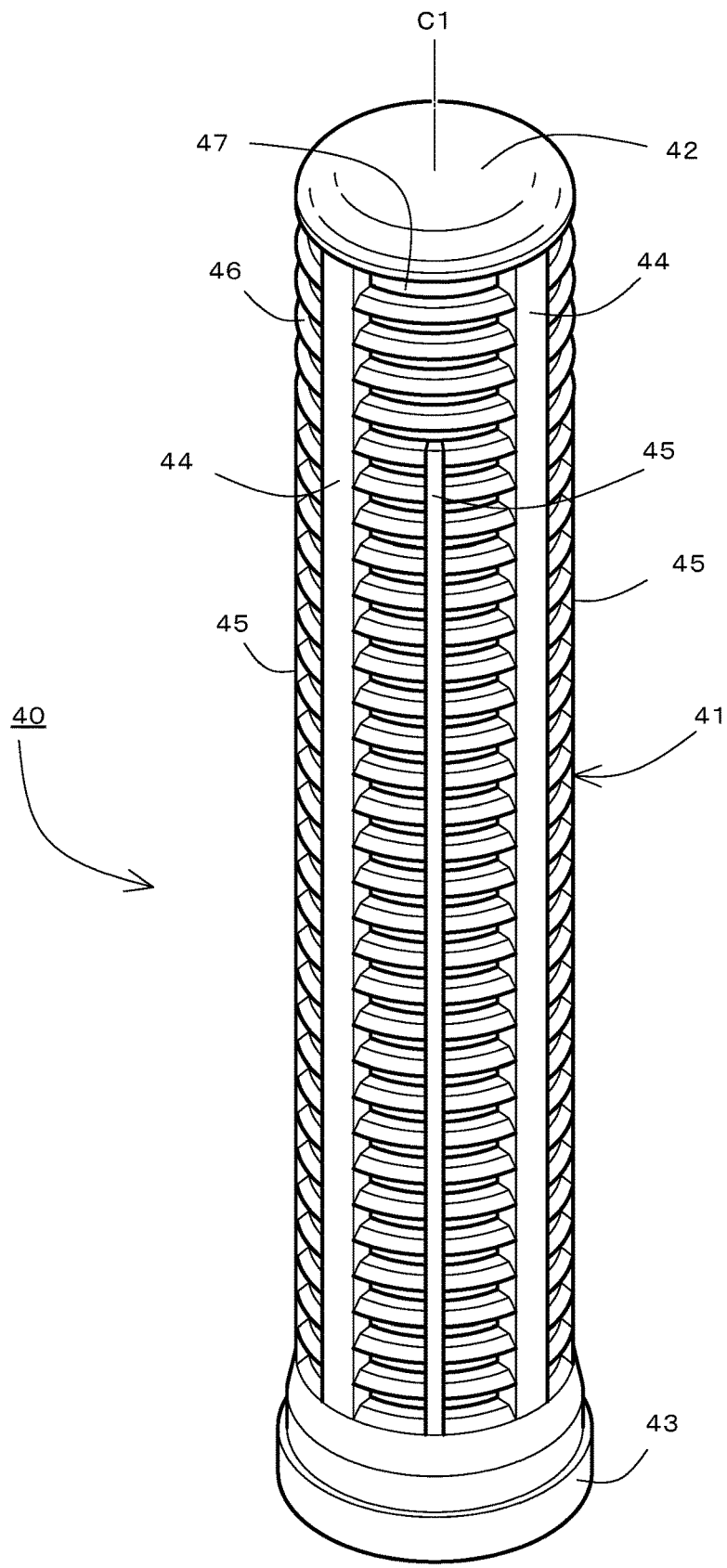
FIG. 7 is a perspective view illustrating a filter provided in the air trap chamber according to the embodiment.
Figure 8:
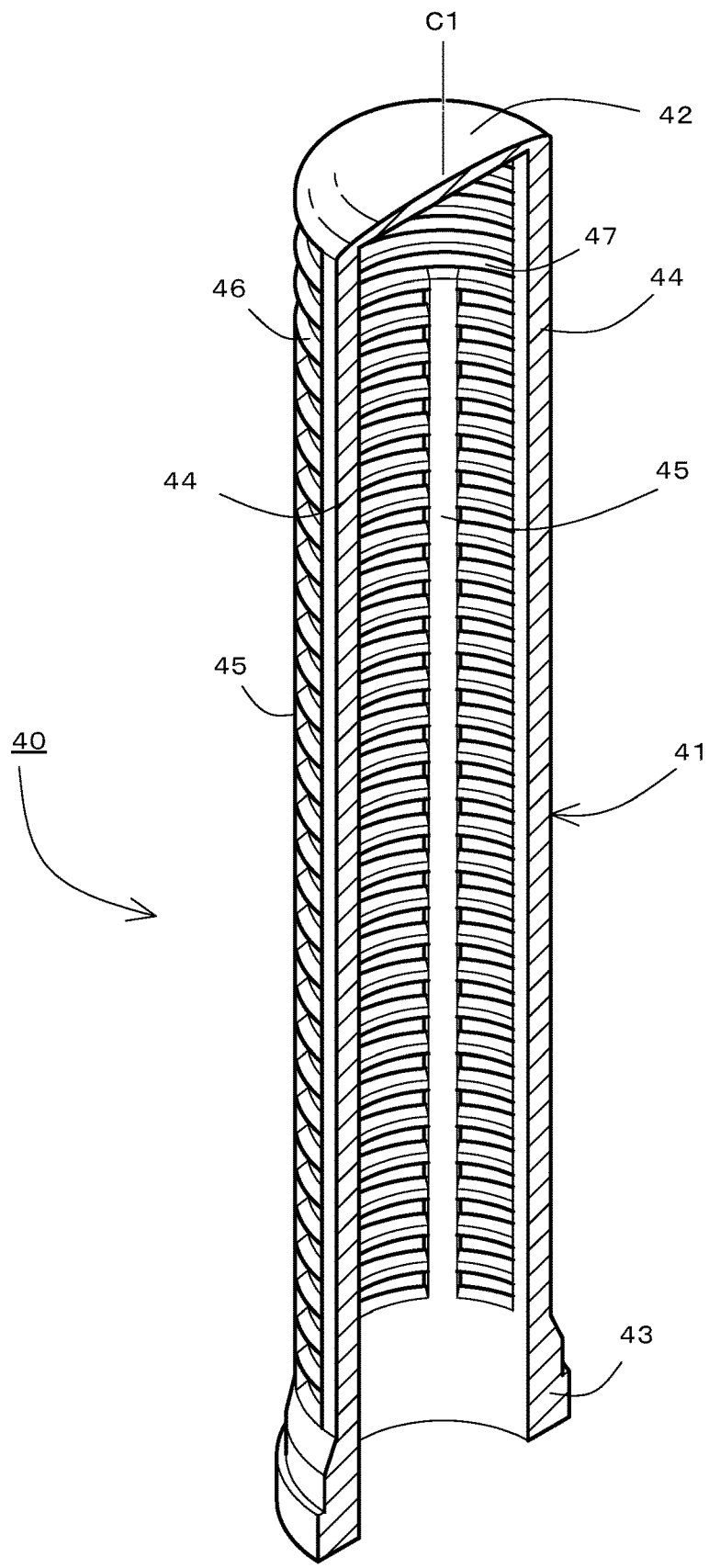
FIG. 8 is a perspective sectional view illustrating the filter provided in the air trap chamber according to the embodiment.

FIG. 7 illustrates the filter 40 according to the embodiment. FIG. 8 illustrates a perspective sectional view of the filter 40. The filter 40 is provided in the chamber body 12 so as to cover the outlet 31 and captures solid matters such as thrombus in blood. The filter 40 is obtained by injection molding a resin, for example. The filter 40 is formed such that the length of the filter 40 in the longitudinal direction (axial direction) is less than the distance between the inlet 23 and the outlet 31. The filter 40 is provided with, for example, a cylindrical body, and a dome-shaped top head provided at the upper end of the body and is hollow as illustrated in FIG. 8. Its lower end is open. The filter 40 includes a cylindrical section 41, a ceiling section 42, and a fixation section 43.

The fixation section 43 is a lower end portion of the filter 40 and is locked in the outlet pipe 33 of the chamber body 12. For instance, as illustrated in FIG. 3, the upper end of the outlet pipe 33 has a tapered shape in which the inner diameter decreases upward, and the outer circumferential surface of the fixation section 43 has a tapered shape (inverse tapered shape) fitted thereto.

When the filter 40 is attached to the chamber body 12, the filter 40 is inserted into the chamber from the outlet 31 so that the ceiling section 42 is inserted first. A tube (not shown in the drawing) coated with a solvent (adhesive) is pushed into a space between the tapered inner circumferential surface of the outlet pipe 33 and the tapered outer circumferential surface of the fixation section 43, thereby positioning the filter 40. At the time of this positioning, the tube is bonded to the inner circumferential surface of the outlet pipe 33 with the solvent. In this way, the tube seals the space between the housing 30 and the filter 40.

The ceiling section 42, which is the upper end section of the filter 40, has a substantially dome shape (hemispherical shape). In other words, the ceiling section 42 covers the upper end of the cylindrical section 41; i.e., the end opening opposite to the lower end on the outlet 31 side of the chamber body 12. Although no opening is provided in the ceiling section 42 in the example shown in FIGS. 7 to 9, this is not necessarily the case and an opening may be provided in any location.

The cylindrical section 41 surrounds the outlet 31 of the chamber body 12 and extends in the direction of the central axis C1 of the chamber body 12. The cylindrical section 41 includes first ribs 44 and second ribs 45 extending in the direction of the central axis C1, and blades 46 extending in the circumferential direction.

The blades 46 are annular members extending in the circumferential direction, and are provided in multiple stages aligned along the central axis of the cylindrical section 41. For instance, in FIGS. 7 and 8, 32 stages of blades are provided. Although there are 32 stages in the examples shown in FIGS. 7 and 8 in order to ensure the resolution of the drawings, more stages may be provided. For instance, the blades 46 may be provided in 10 or more stages; for example, across 40 stages.

Each first rib 44 is a skeleton member that extends from the fixation section 43, which is the lower end of the filter 40, to the ceiling section 42, which is the upper end of the filter 40. For instance, four first ribs 44 are provided about the central axis of the cylindrical section 41 at 90° intervals in the circumferential direction.

Each second rib 45 is a skeleton member that reinforces the first rib 44, and extends from the fixation section 43, which is the lower end of the filter 40, and is terminated before reaching the ceiling section 42, which is the upper end of the filter 40. For instance, in the example shown in FIG. 7, the upper ends of the second ribs 45 are coupled to the 28th stage, which is, from the bottom, 87.5% (⅞) of the total number (32 stages) of blades 46. In other words, openings 47 in up to the fourth stage from the top, which is 12.5% (⅛) of the total number of stages of blades 46, are widened.

Four second ribs 45 are provided, for example, about the central axis of the cylindrical section 41 at 90° intervals in the circumferential direction, deviated by 45° from the first ribs 44. The upper ends of all the four second ribs 45 are coupled to the blades 46 at the 28th stage from the bottom.

The first ribs 44 and second ribs 45 extending in the direction of the central axis of the cylindrical section 41 and the multi-stage blades 46 extending in the circumferential direction intersect, so that multi-stage openings 47 (see FIG. 9) are formed along the central axis C1 of the chamber body 12 in the cylindrical section 41 of the filter 40.

The openings 47 are formed such that the circumferential length; i.e., the opening width W1, is longer than the length in the direction of the central axis of the cylindrical section 41; i.e., the opening height H1. In particular, the distance between the blades 46, 46 adjacent in the height direction is shorter than the distance between the first rib 44 and the second rib 45 adjacent in the circumferential direction.

When such a so-called laterally long opening 47 is used, the minimum diameter of solid matters in blood that can be captured by the filter 40 depends on the opening height H1 of the opening 47. For example, the opening height H1 of the opening 47 may be in the range of 0.2 mm to 0.4 mm, preferably 0.35 mm.

Figure 9:
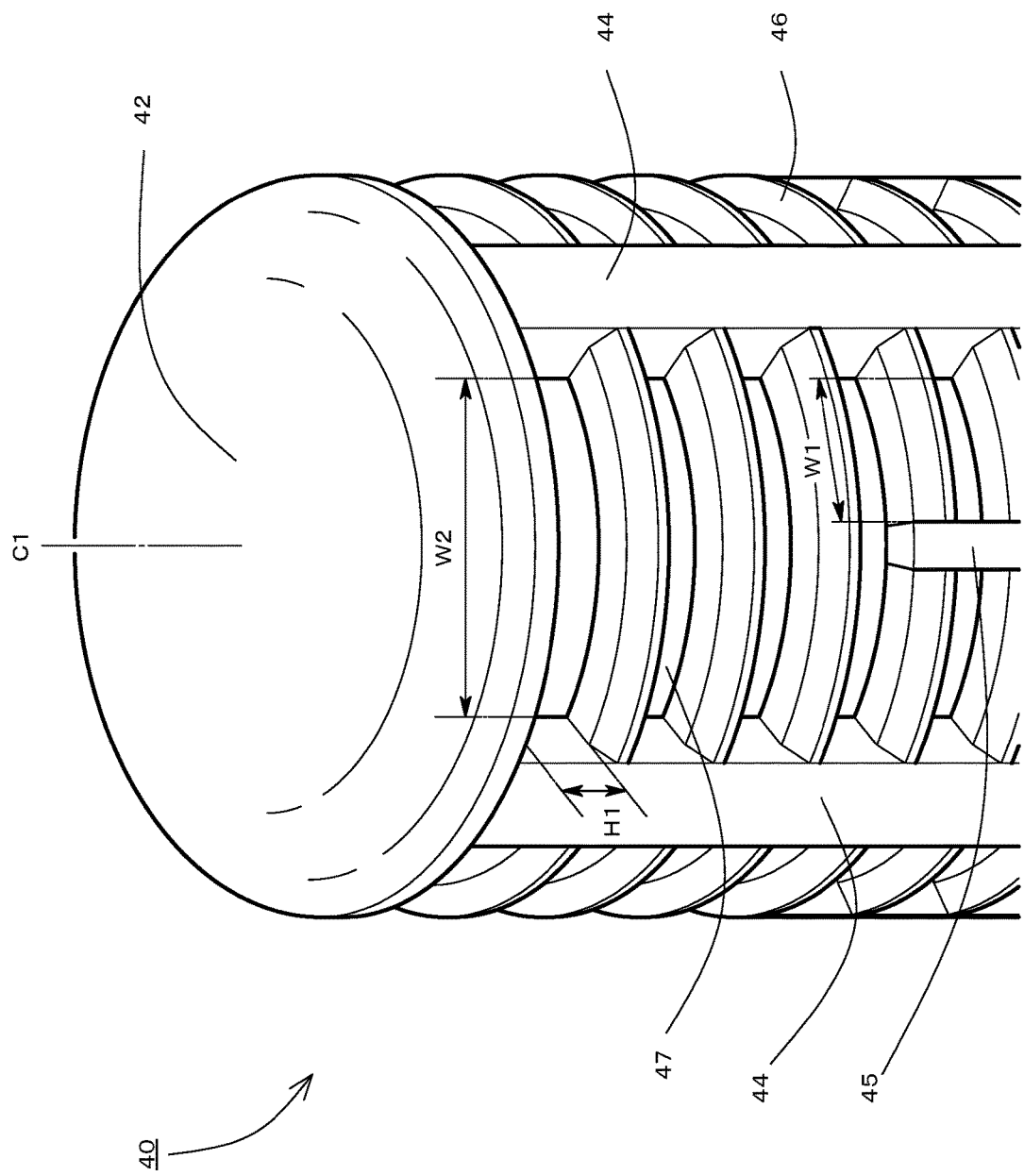
FIG. 9 is an enlarged perspective view illustrating the filter provided in the air trap chamber according to the embodiment.

Referring to FIG. 9, in the filter 40 according to the present embodiment, the second ribs 45 terminate before reaching the ceiling section 42. As a result, among the openings 47 of the filter 40, in the opening 47 in the upper stage adjacent to the ceiling section 42, specifically, in the opening 47 in a stage above the end point of the second ribs 45, the circumferential width W2 is made larger than the circumferential width W1 of the opening 47 in a lower stage (W2>W1).

To be specific, in a lower region in which the second ribs 45 are extended, the circumferential width W1 of an opening 47 is defined by the distance between a first rib 44 and the second rib 45 adjacent to it in the circumferential direction. For instance, the opening 47 has an opening angle of 45° with respect to the central axis of the cylindrical section 41.

On the other hand, in the opening 47 in a stage above the blade 46 where the second ribs 45 terminate, its circumferential width W2 is defined by the distance between the first ribs 44, 44 adjacent in the circumferential direction. For instance, the opening 47 has an opening angle of 90° with respect to the central axis of the cylindrical section 41.

In this way, with a structure in which the circumferential width W2 of the opening 47 in an upper stage of the filter 40 is larger than the circumferential width W1 of the opening 47 in a lower stage, the flow resistance of a liquid (blood and saline solution) having a relatively low flow velocity and flowing into the opening 47 in the upper stage can be reduced, thereby preventing retention. The direction in which the opening 47 extends is the circumferential direction along the swirl flow, which particularly effectively contributes to a reduction in the flow resistance.

Note that the multiple openings 47 may be formed so that the relation of the total opening area A1 of the multiple openings 47 having the opening width W2 with respect to the total area A of all the openings 47 of the filter 40 is A1≥0.15 A.

Figure 10:
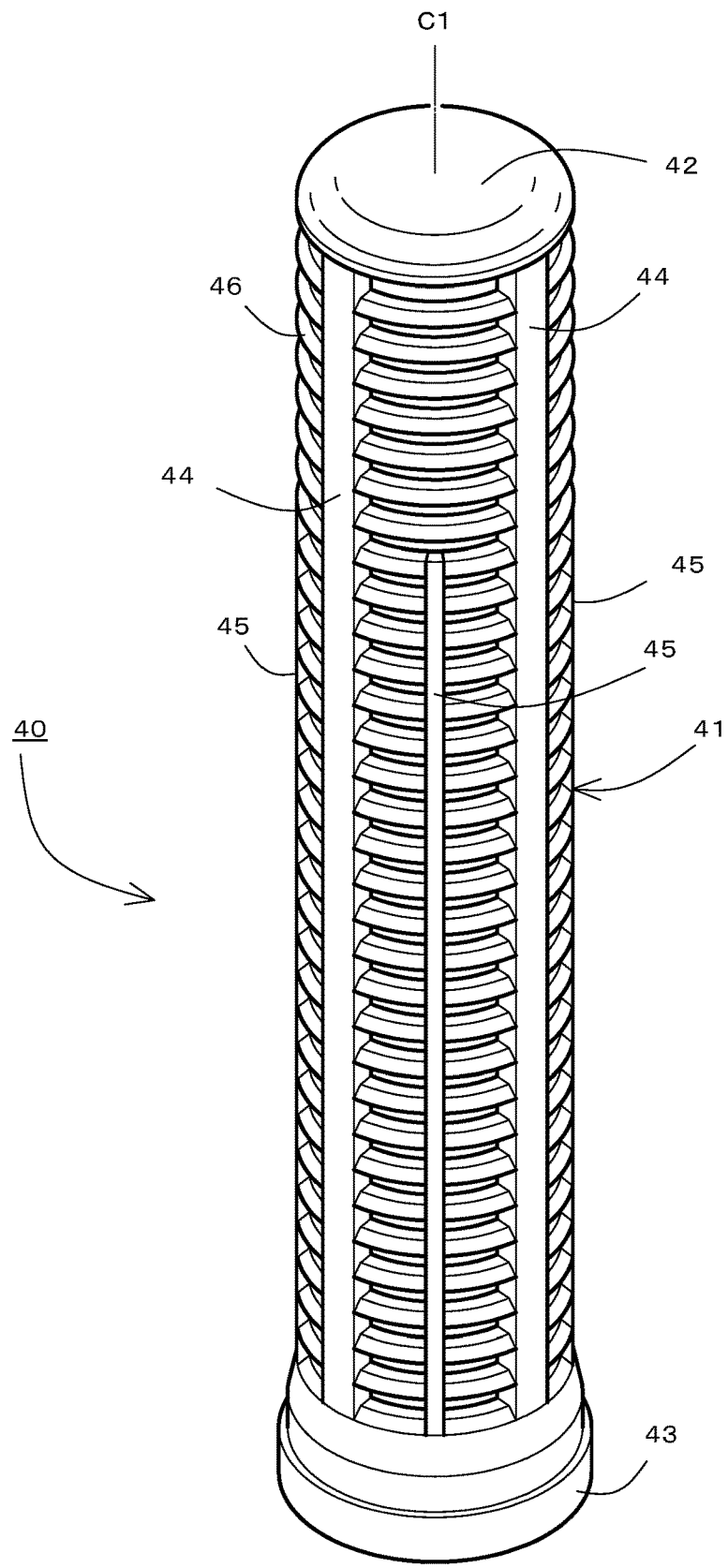
FIG. 10 is a perspective view illustrating another example of a filter provided in the air trap chamber according to the embodiment.
Figure 11:
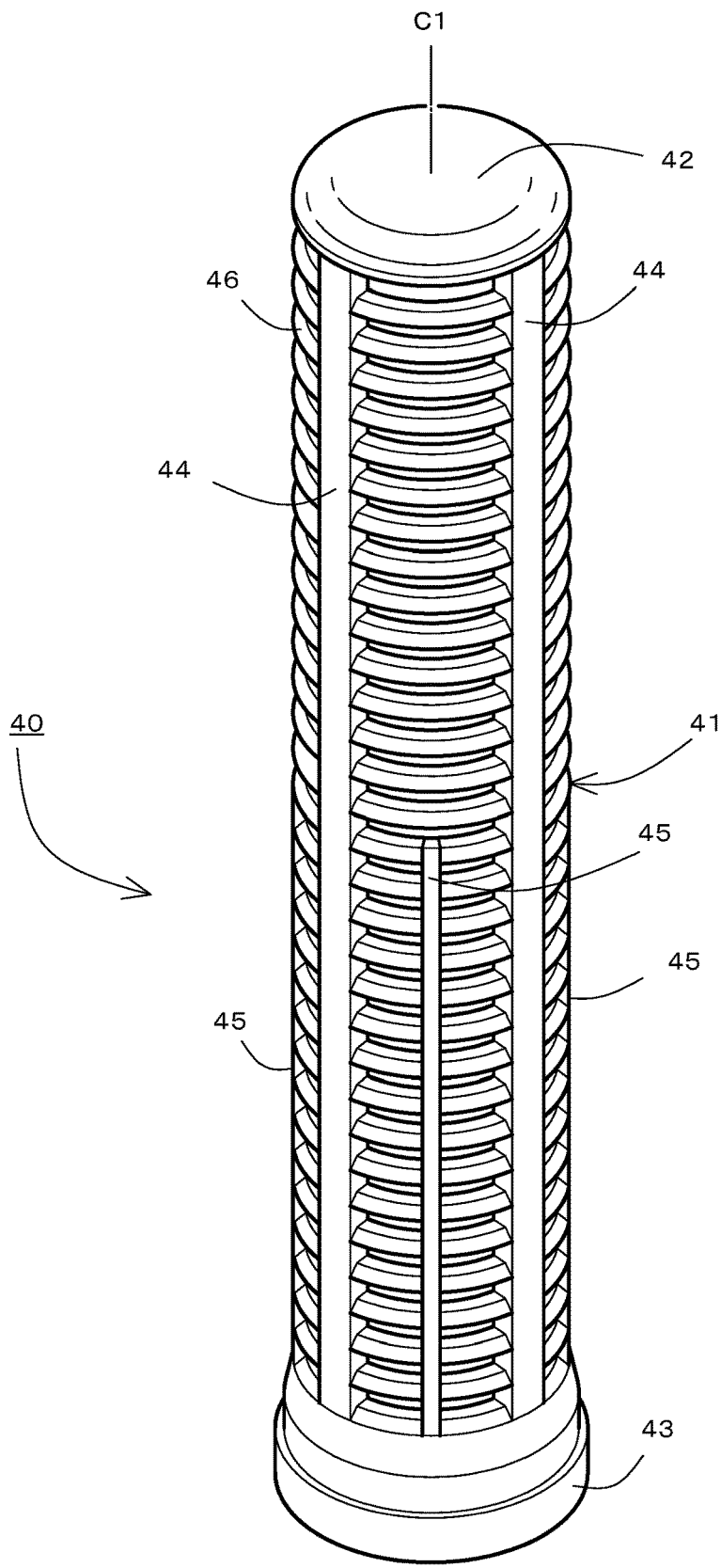
FIG. 11 is a perspective view illustrating still another example of a filter provided in the air trap chamber according to the embodiment.

FIGS. 10 and 11 show modified examples (first modified example and second modified example) of the filter 40 according to the present embodiment. In the filter 40 according to the first modified example shown in FIG. 10, the end points of the second ribs 45 are located lower than in the example of FIG. 7. To be specific, the end points of the second ribs 45, which are the upper ends of the second ribs 45, are coupled to the blades 46 in the 24th stage from the bottom; i.e., the blades 46 at 75% (¾) of the total number (32 stages). In other words, the openings 47 in up to the eighth stage from the top, which is at 25% (¼) of the total number of stages of blades 46, are widened.

In the filter 40 according to the second modified example shown in FIG. 11, the end points of the second ribs 45 are located even lower than in the first modified example of FIG. 10. To be specific, the end points of the second ribs 45, which are the upper ends of the second ribs 45, are coupled to the blades 46 in the 16th stage from the bottom; i.e., the blades 46 at 50% (½) of the total number (32 stages). In other words, the openings 47 in up to the 16th stage from the top, which is at 50% of the total number of stages of blades 46, are widened.

Similarly to the example shown in FIG. 7, in the filter 40 according to the first and second modified examples, the circumferential width of a relatively upper opening 47 is widened from that of a lower opening 47. It is therefore possible to reduce the flow resistance when a liquid flowing above the filter 40 and swirling at a relatively low flow velocity passes through the opening 47 with the widened width.

Figure 12:
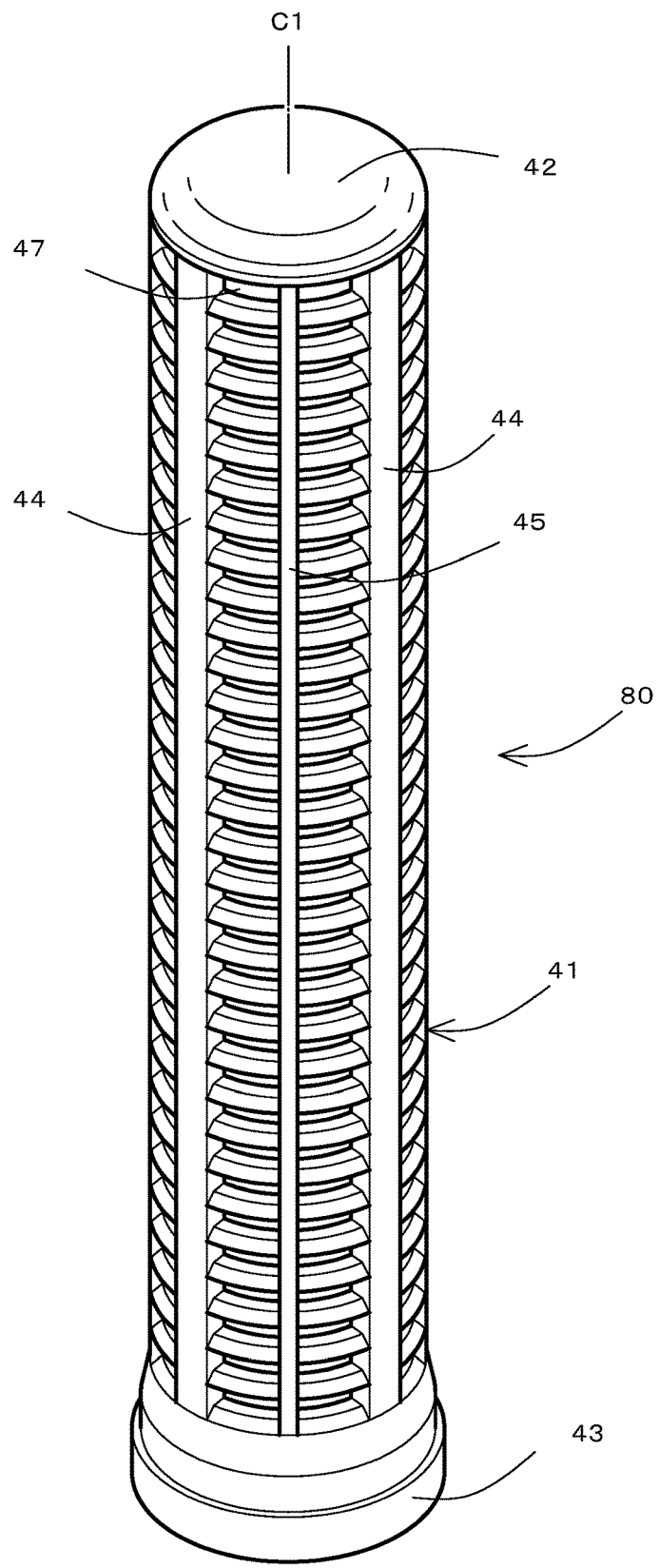
FIG. 12 is a perspective view illustrating a comparative example of a filter.

The effect of reducing the flow resistance using the filter 40 according to this embodiment will be described with reference to FIGS. 12 to 16. FIG. 12 illustrates a filter 80 as a comparative example. In this example, similarly to the first ribs 44, the second ribs 45 also extend from the lower end to the upper end of the cylindrical section 41; that is, from the fixation section 43 to the ceiling section 42. In the filter 80 according to this comparative example, all the openings 47 have uniform dimensions including the circumferential width.

FIGS. 13 to 16 illustrate fluid analysis results for the filter 40 according to the embodiment and the filter 80 according to the comparative example. In the fluid analysis, the total areas of the openings 47 of all the filters are made equal. For instance, for all the filters, the total area of the openings 47 is 115 mm².

Figure 13:
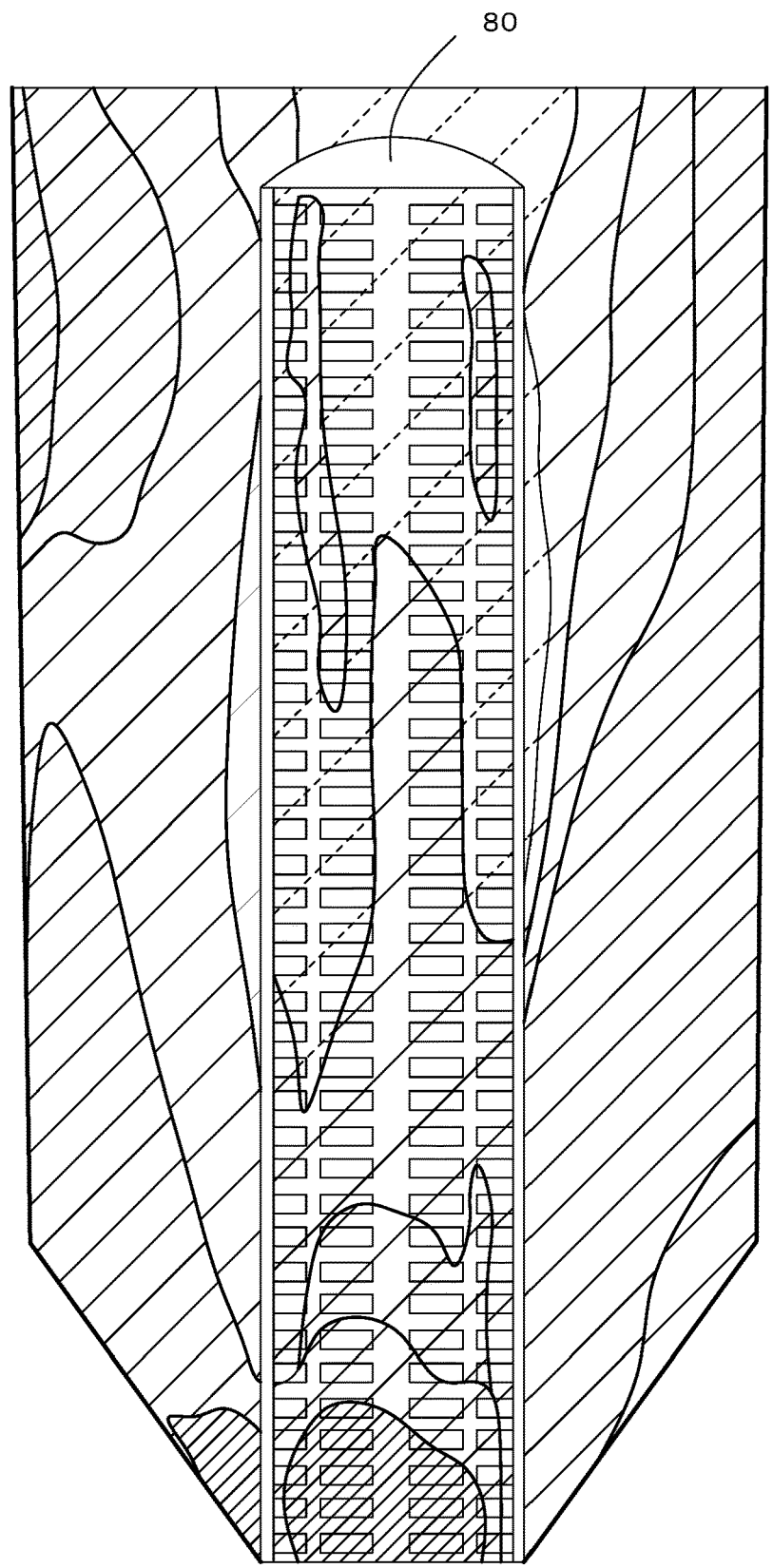
FIG. 13 is a diagram illustrating a flow rate distribution in the vicinity of a filter during use of the filter according to the comparative example.
Figure 14:
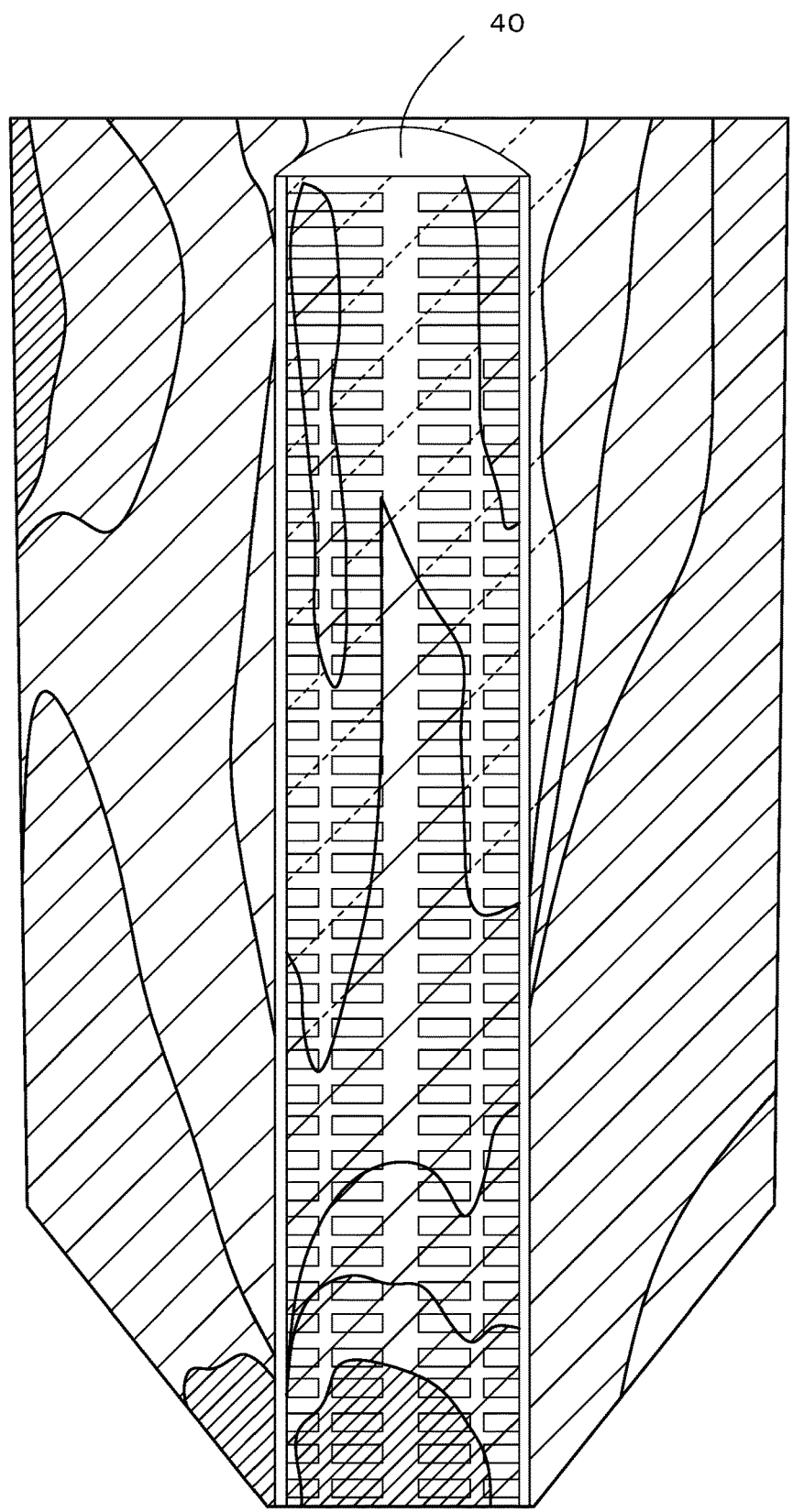
FIG. 14 is a diagram illustrating a flow rate distribution in the vicinity of a filter during use of the filter according to the embodiment.
Figure 15:
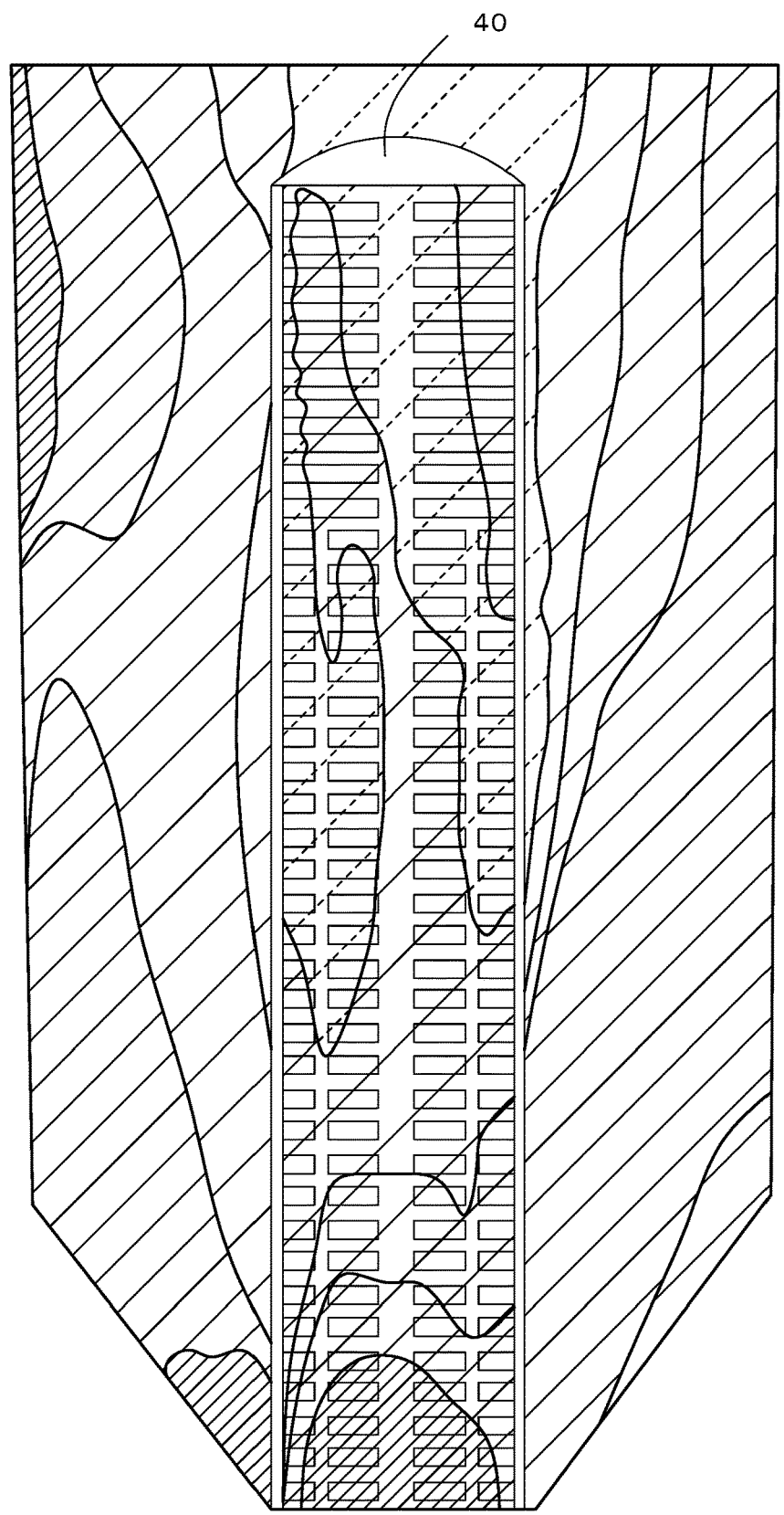
FIG. 15 is a diagram illustrating a flow rate distribution in the vicinity of a filter during use of the filter according to another example of the embodiment.
Figure 16:
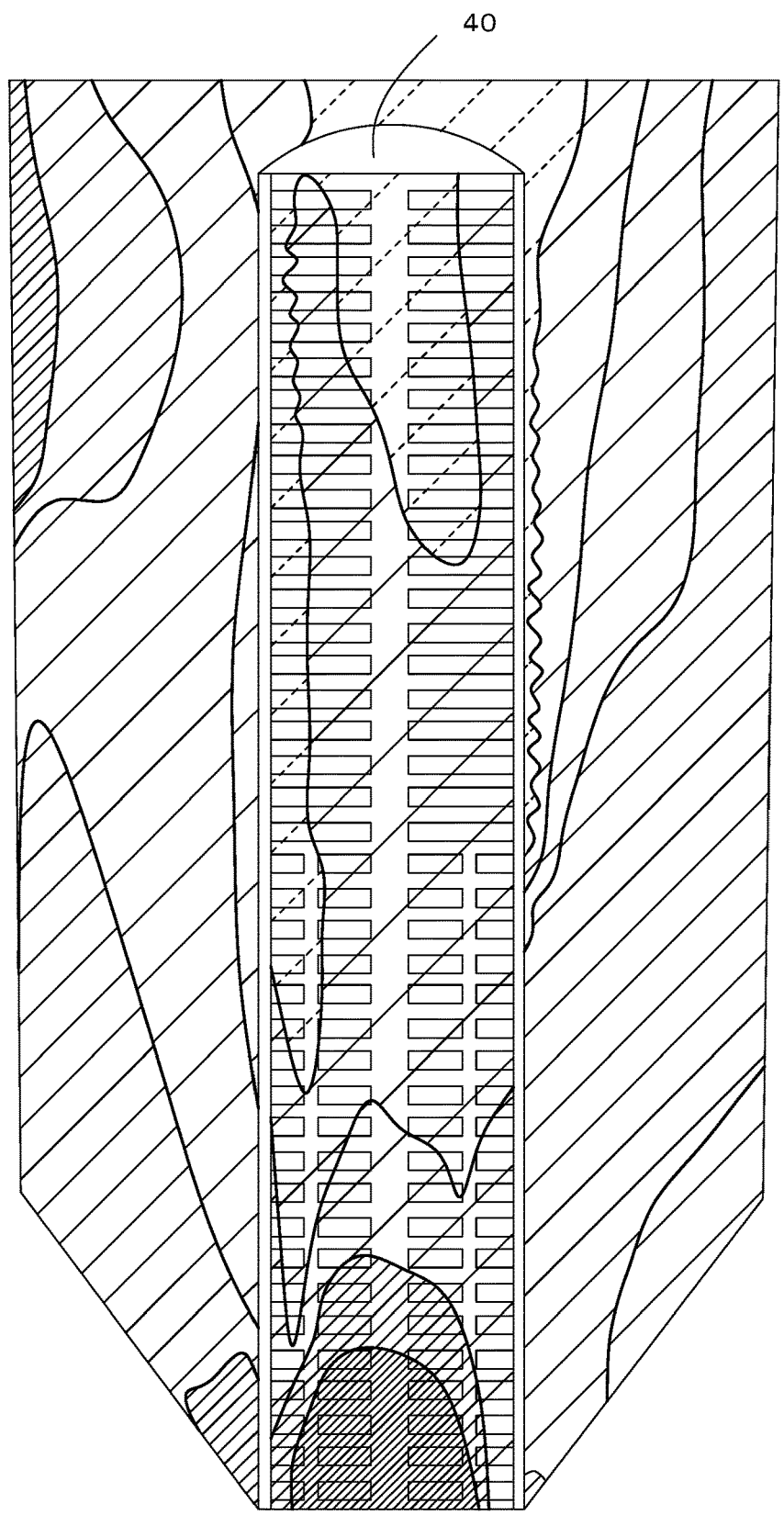
FIG. 16 is a diagram illustrating a flow rate distribution in the vicinity of a filter during use of the filter according to a still another example of the embodiment.

Note that FIG. 13 shows a fluid analysis result for the filter 80 according to the comparative example. FIG. 14 shows a fluid analysis result for the filter 40 (upper stage width 12.5% widened) shown in FIG. 7. FIG. 15 shows a fluid analysis result for the filter 40 (upper stage width 25% widened) shown in FIG. 10 (first modified example). FIG. 16 shows a fluid analysis result for the filter 40 (upper stage width 50% widened) shown in FIG. 11 (second modified example).

The analysis results shown in FIGS. 13 to 16 all show an example in which the filter 40 and its peripheral region are partitioned by the flow rate [m³/s]. Here, the higher the flow rate, the smaller the pitch of the hatching. Further, for clarity, the region with the lowest flow rate is hatched with dashed lines.

FIGS. 13 to 16 show that the region with the lowest flow rate is distributed above the filters 40 and 80. FIGS. 13 to 16 show that the region with the minimum flow rate narrows with an increasing number of stages in which the circumferential width of the openings 47 is widened. As described above, in this embodiment, in a region above the filter 40 where the flow rate is relatively low, the circumferential width of the opening 47 is made wider than the circumferential width of the opening 47 in the lower stage, thereby reducing the flow resistance and therefore suppressing the retention of the liquid in the air trap chamber 10.

<Still Another Example of Filter>

Figure 17:
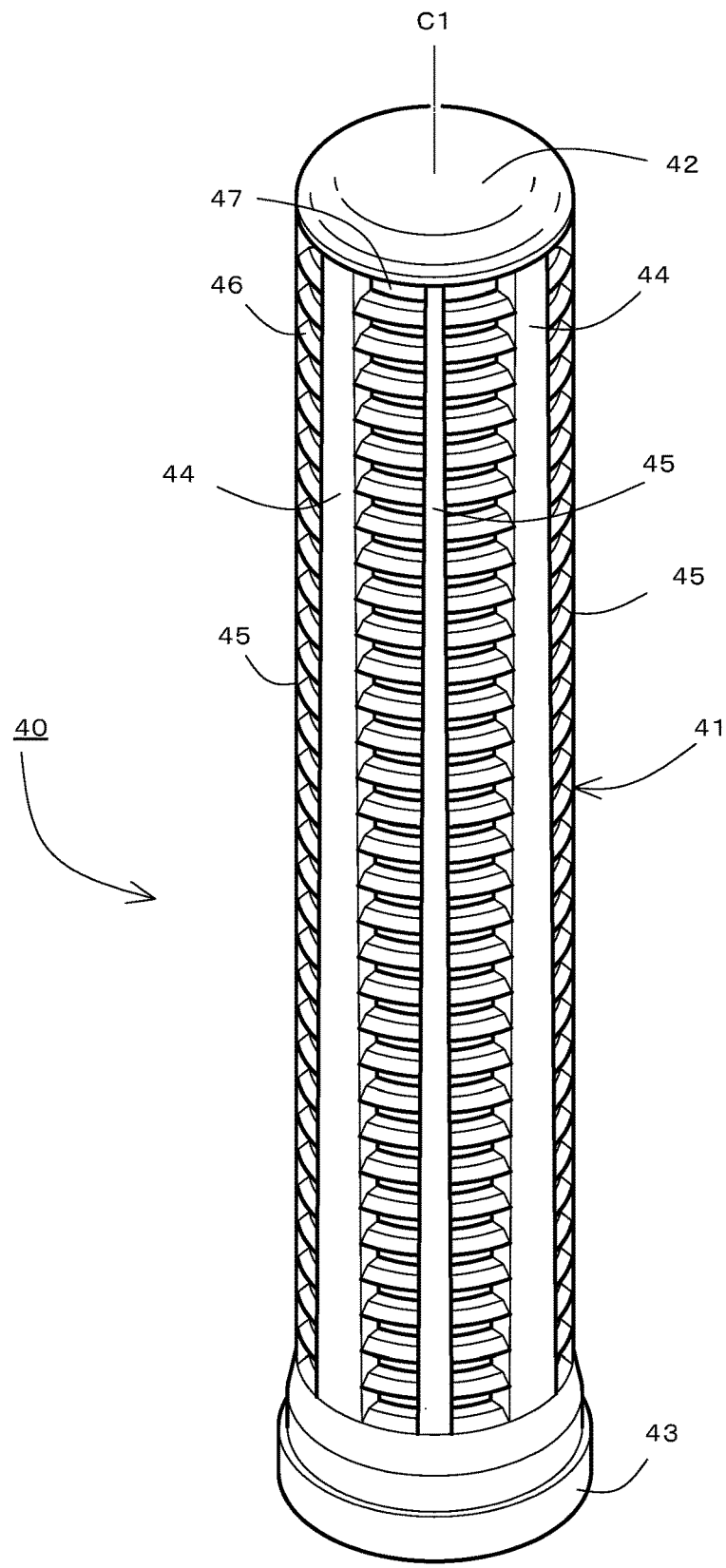
FIG. 17 is a perspective view illustrating a filter according to yet another example of the embodiment.

FIG. 17 illustrates still another example (third modified example) of the filter 40 according to the embodiment. In this example, as in FIG. 7, both the first ribs 44 and the second ribs 45 extend in the direction of the central axis of the cylindrical section 41, and the first ribs 44 and the second ribs 45 extend in the circumferential direction. It is however different from FIG. 7 in that both the first ribs 44 and the second ribs 45 extend from the lower end to the upper end of the cylindrical section 41. In particular, the first ribs 44 and the second ribs 45 extend from the fixation section 43 to the ceiling section 42. In addition, the first ribs 44 and the second ribs 45 have a tapered shape in which the circumferential width is narrowed from the lower end (fixation section 43) to the upper end (ceiling section 42) of the filter 40.

With such a tapered shape, the distance between the first rib 44 and the second rib 45 adjacent to each other increases upward. In other words, the circumferential width of the opening 47 is widened upward. With such a configuration also, in a region above the filter 40 where the flow rate is relatively low, the circumferential width of the opening 47 can be made larger than the circumferential widths of the openings 47 in the lower stages. Accordingly, the flow resistance of a liquid passing through the region above the filter 40 can be reduced, and retention of the liquid in the air trap chamber 10 can be prevented.

REFERENCE SIGNS LIST

10 Air trap chamber, 12 Chamber body, 20 Cap, 21 Inlet pipe, 22 Air vent, 23 Inlet, 25 Cap body, 26 Cap body inner circumferential surface, 30 Housing, 31 Outlet, 33 Outlet pipe, 40 Filter, 41 Cylindrical section, 42 Ceiling section, 43 Fixation section, 44 First rib, 45 Second rib, 46 Blade, 47 Opening, 50 Arterial side circuit, 51 Venous side circuit, 54 Blood purifier, 55 Dialyzer

The invention claimed is:

1. An air trap chamber comprising:
a chamber body that has a substantially cylindrical shape, has an inlet pipe at one end with respect to a direction of a central axis of the chamber body and an outlet at another end, and in which a liquid flows down from the inlet pipe to the outlet downward, wherein
the inlet pipe is extended into the chamber body and an inlet, an end opening of the inlet pipe, is provided at an inner circumferential surface of the chamber body and faced in a circumferential direction,
a filter covering the outlet is provided in the chamber body,
the filter includes:
a cylindrical section that surrounds the outlet and extends in the direction of the central axis of the chamber body,
a ceiling section that covers an upper end of the cylindrical section, the upper end opposite to a lower end of the chamber body, the lower end being adjacent to the outlet, the cylindrical section of the filter has openings in multiple stages aligned in the direction of the central axis, a circumferential width of one of the openings in an upper stage of the multiple stages adjacent to the ceiling section of the filter is made larger than a circumferential width of another opening in a lower stage of the multiple stages adjacent to the outlet, the filter is provided with multiple ribs that extend in the direction of the central axis of the chamber body and are aligned along the circumferential direction, and the multiple ribs include:
  a first rib that extends from a lower end of the filter to the ceiling section of the filter; and
  a second rib that extends from the lower end of the filter and terminates before reaching the ceiling section of the filter.

2. The air trap chamber according to claim 1, wherein
the circumferential widths of the ribs decrease from a lower end of the filter toward the ceiling section of the filter.

3. An extracorporeal circulation circuit that circulates removed blood and has a flow path coupled to the air trap chamber according to claim 1.

* * * * *